(12) United States Patent
Zille (10) Patent No.: US 12,426,902 B2
(45) Date of Patent: Sep. 30, 2025

(54) SURGICAL CUTTING GUIDES DESIGNED FOR ANATOMICAL LANDMARKS

(71) Applicant: OsteoMed LLC, Addison, TX (US)

(72) Inventor: Devid R. Zille, Addison, TX (US)

(73) Assignee: OsteoMed LLC, Addison, TX (US)

( * ) Notice: Subject to any disclaimer, the term of this patent is extended or adjusted under 35 U.S.C. 154(b) by 454 days.

(21) Appl. No.: 17/006,603

(22) Filed: Aug. 28, 2020

(65) Prior Publication Data

US 2021/0059691 A1    Mar. 4, 2021

Related U.S. Application Data

(60) Provisional application No. 62/893,729, filed on Aug. 29, 2019.

(51) Int. Cl.
*A61B 17/17* (2006.01)
*A61B 17/15* (2006.01)
*B33Y 80/00* (2015.01)

(52) U.S. Cl.
CPC .......... *A61B 17/176* (2013.01); *A61B 17/151* (2013.01); *B33Y 80/00* (2014.12)

(58) Field of Classification Search
CPC ....... A61B 17/17; A61B 17/176; A61B 17/15; A61B 17/151; B33Y 80/00; B33Y 50/02
See application file for complete search history.

(56) References Cited

U.S. PATENT DOCUMENTS

| | | | |
|---|---|---|---|
| 2012/0029574 A1* | 2/2012 | Furrer | A61B 17/151 606/280 |
| 2014/0149095 A1* | 5/2014 | Davison | A61B 17/1728 703/7 |
| 2019/0223988 A1* | 7/2019 | Palmer | A61C 1/084 |
| 2020/0129213 A1* | 4/2020 | Singh | A61B 17/1662 |
| 2020/0281655 A1* | 9/2020 | Cen | B29C 64/393 |

OTHER PUBLICATIONS

U.S. Appl. No. 16/378,446, OsteoMed LLC.

* cited by examiner

*Primary Examiner* — Christopher J Beccia
(74) *Attorney, Agent, or Firm* — Knobbe, Martens, Olson & Bear, LLP (57) ABSTRACT

The present application describes various embodiments of guides that are designed in accordance with one or more anatomical landmarks near an operated bone (or portion thereof). In aspects, at least a portion of a guide is designed to conform to the shape of one or more anatomical landmarks in order to attach (or latch) the guide to at least one of the one or more anatomical landmarks. In aspects, the contact surface (or inner contour) of a guide may also be designed to follow at least a portion of the contour of the operated bone. The landmark-conforming and/or contour-following design of the guide may assist surgeons in the placement of the guide.

20 Claims, 7 Drawing Sheets

SURGICAL CUTTING GUIDES DESIGNED FOR ANATOMICAL LANDMARKS

CROSS-REFERENCE TO RELATED APPLICATIONS

The present application claims priority to U.S. Provisional Application No. 62/893,729 filed Aug. 29, 2019 and entitled "SURGICAL CUTTING GUIDES DESIGNED FOR ANATOMICAL LANDMARKS," the disclosure of which is incorporated by reference herein in its entirety.

TECHNICAL FIELD

The present disclosure generally relates to osteotomy procedures, including methods and systems employed in such procedures. In particular, the disclosure describes surgical cutting guides designed in accordance with anatomical landmarks identified before performing the procedure.

BACKGROUND

An osteotomy procedure is generally performed to correct bone-related defects and/or abnormalities. The procedure may include a surgical operation where a surgeon (e.g., an orthopedic surgeon) operates on a bone to bring change to its underlying structure (e.g., changing its length or alignment). An illustrative osteotomy procedure may include surgically cutting or dividing the tibia bone (or a portion thereof) and then shifting the divided ends to change the alignment of the tibia bone. Another illustrative osteotomy procedure may include transverse sectioning and repositioning the maxilla. Yet another illustrative osteotomy procedure may include excising a tumor from a bone and, in some cases, replacing the excised bone with an implant structure.

Surgeons may employ different types of techniques to perform osteotomy procedures. Some surgeons use a freehand technique where they perform the procedure, manually, without the aid of guiding instruments. However, the freehand technique is technically demanding, can lead to inaccuracies (e.g., inaccurate cuts), and may result in undesired surgical outcomes, such as fractures, gap formation, angulation, inadequate length of excision, misalignment of the implant against the bone, and poor coaptation of the junction surface. To prevent errors and to improve precision, some surgeons use devices, such as surgical cutting guides, while performing the procedures. A surgical cutting guide (hereinafter referred to as "guide") is a stencil-like customized tool made from a sterilizable material. These guides have cutting slots and other relevant markings on them that assist surgeons in sawing and/or drilling the bone in the desired direction and for the desired length, thereby improving the quality of the procedure.

Figure 1:
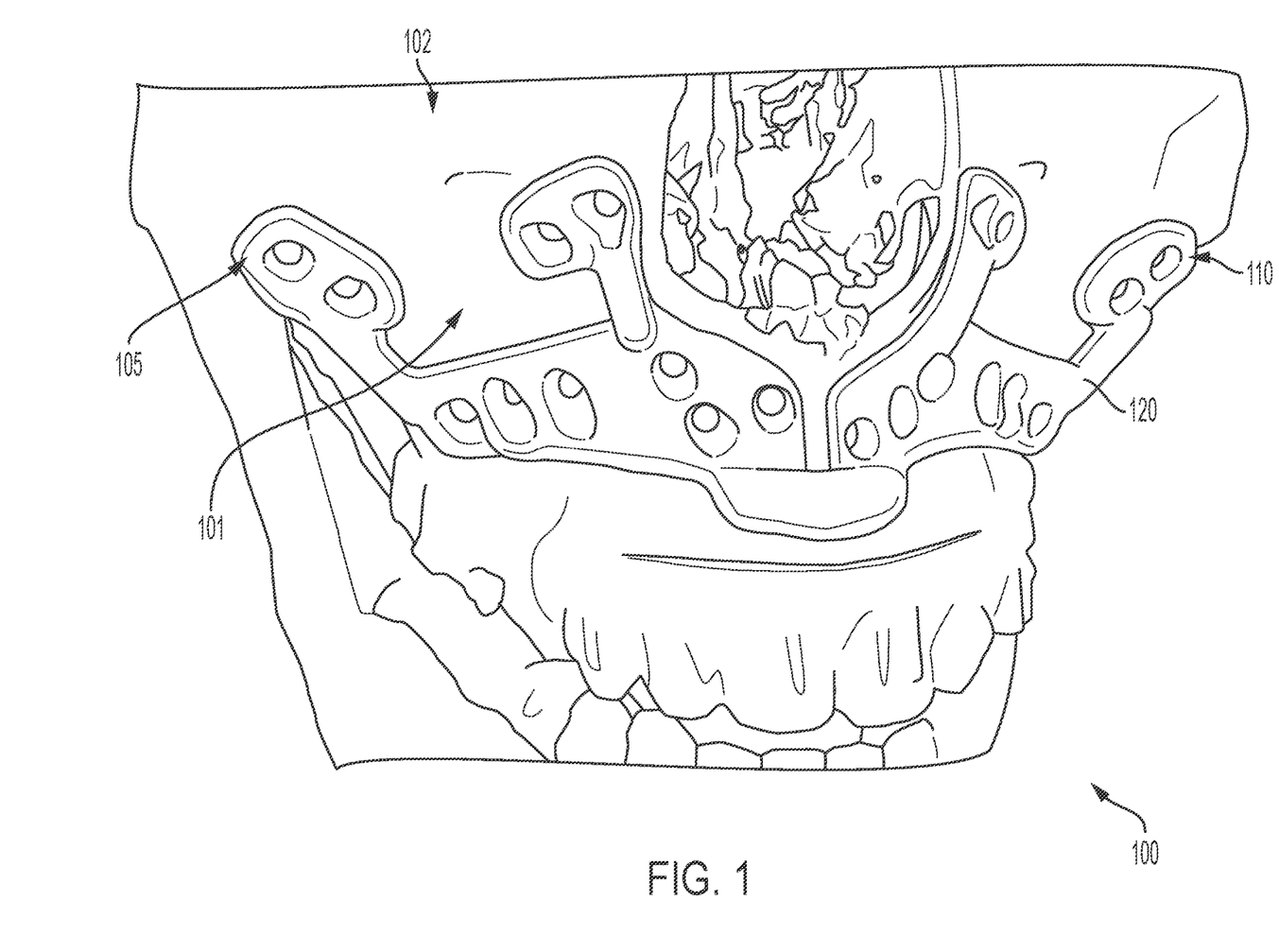
FIG. 1 depicts a prior art surgical cutting guide.

However, it can be challenging for surgeons to accurately position a guide at a desired location over the operated bone. This can be because, during surgery, the surgeon may find it difficult to locate the precise location and angle to position the guide on the exposed bone. To avoid such placement errors, the guides are generally designed to encompass a whole curvature of the underlying bone, where both the ends of the curvature of the bone and the shape of the guide relative to the curvature of the underlying bone are used by surgeons as quasi reference locations to affix—using surgical screws and wires—the guide to the underlying bone. Once affixed, the slots and marking on the guide position themselves at the desired location on the underlying bone. For example, see FIG. 1, a three dimensional (3D) rendered image 100 of a portion of a skull 102. FIG. 1 depicts a guide 120 placed on maxilla bone 101. While performing a procedure on the maxilla bone 101, the surgeon first exposes a large portion of the maxilla bone 101, and then affixes the left end 105 of the guide 120 to the left zygomatic bone and the right end 110 of the guide 120 on the right zygomatic bone, while ensuring that the middle portion of the guide 120 symmetrically surrounds the nasal aperture. In doing so, the surgeon positions the slots and marking of the guide 120 at the desired location on the maxilla bone 101. However, the guides designed this way encompass a large part of the curvature of the maxilla 101 and affix the guide at multiple points, which make the guides bulky. In some cases, the bulkiness is adverse as it may interfere during surgery, may require additional tissue detachments, and may result in swelling.

SUMMARY

The present application describes various embodiments of guides that are designed in accordance with one or more anatomical landmarks near the bone (or portion thereof) on which the surgeon wants to operate. In aspects, at least a portion of a guide is designed to conform to the shape of one or more anatomical landmarks in order to attach (or latch) the guide to at least one of the one or more anatomical landmarks. In aspects, the contact surface (or inner contour) of a guide may also be designed to follow at least a portion of the contour of the bone on which the surgeon wants to operate. The landmark-conforming and/or contour-following design of the guide may assist surgeons in the placement of the guide. Thus, once identified, the anatomical landmarks act as reference locations (or locations of attachment) and facilitate designing and manufacturing of the guides that are relatively smaller in size, encompass a relatively small part of the underlying bone, and are relatively less bulky.

Some embodiments described in this application provide for patient-specific guides. In such embodiments, the anatomical landmarks that are identified to be utilized as reference points are also patient-specific. In aspects, patient-specific guides may be custom designed individually for every patient according to the patient's anatomical model (which is created from various medical imaging techniques (e.g., CT scans, MM scans, and the like)). In aspects, the anatomical landmarks may often be identified before manufacturing the guide and operating on the patient.

Some embodiments described in this application provide for non-patient specific guides. These guides are not designed for a specific patient, but are designed in accordance with specific anatomical landmarks generally found in the human anatomical structure. The specific anatomical landmarks found in human anatomical structure may vary with certain demographic characteristics (e.g., age, gender). As such, in aspects, the design of the non-patient specific guides may be based on age, gender, and the like. In aspects, a non-patient specific design of the guides can be used to produce multiple guides and can further be used in osteotomy procedures of different patients.

The present application also describes various embodiments of methods for manufacturing these guides. For the embodiments associated with patient-specific guides, the manufacturing process may include receiving a patient's imaging data (e.g., CT scans, MM scans, and the like). The manufacturing process may also include generating a model using the imaging data and fabricating the guide using the model and/or the imaging data. For embodiments associated with non-patient specific guides, the manufacturing process may include receiving imaging data and/or models of a reference patient and then fabricating the guide using the model and/or the imaging data. In either scenario, the guides may be manufactured using additive manufacturing (e.g. 3D printing) techniques, and the like.

The foregoing has outlined rather broadly the features and technical advantages of the embodiments in order that the detailed description of the embodiments that follows may be better understood. Additional features and advantages of the embodiments disclosed in this application will be described hereinafter which form the subject of the claims of the application. It should be appreciated by those skilled in the art that the conception and specific embodiment disclosed may be readily utilized as a basis for modifying or designing other structures for carrying out the same purposes of the present application. It should also be realized by those skilled in the art that such equivalent constructions do not depart from the spirit and scope of the embodiments in this application as set forth in the appended claims. The novel features which are believed to be characteristic of the embodiments, both as to its organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present disclosure.

BRIEF DESCRIPTION OF THE DRAWINGS

For a more complete understanding, reference is now made to the following descriptions taken in conjunction with the accompanying drawings, in which.

DETAILED DESCRIPTION

Anatomical landmarks may be points or locations of interest on the human body or the skeletal system where guides can be placed in a fitted manner and/or attached (or latched) without being explicitly secured using fixating devices (e.g., wires or surgical screws). For the sake of illustration and clarity, this disclosure describes the guides that may be used during maxilla- and mandible-related osteotomy procedures. Therefore, the anatomical landmarks identified and described in this disclosure are near the maxilla and mandible. However, it should be appreciated that the disclosure is not intended to be limited to the examples and designs of guides used for maxilla and mandible-related procedures, but is to be accorded the widest scope consistent with the principles and novel features of the guides disclosed ahead. Thus, the description ahead is provided to enable any person skilled in the art to make or use the disclosure. Various modifications to the disclosure will be readily apparent to those skilled in the art, and the generic principles of the use and manufacturing of the guides defined herein may be applied to other variations as well (e.g., using guides on other anatomical locations having different anatomical landmarks/features near them).

Figure 2A:
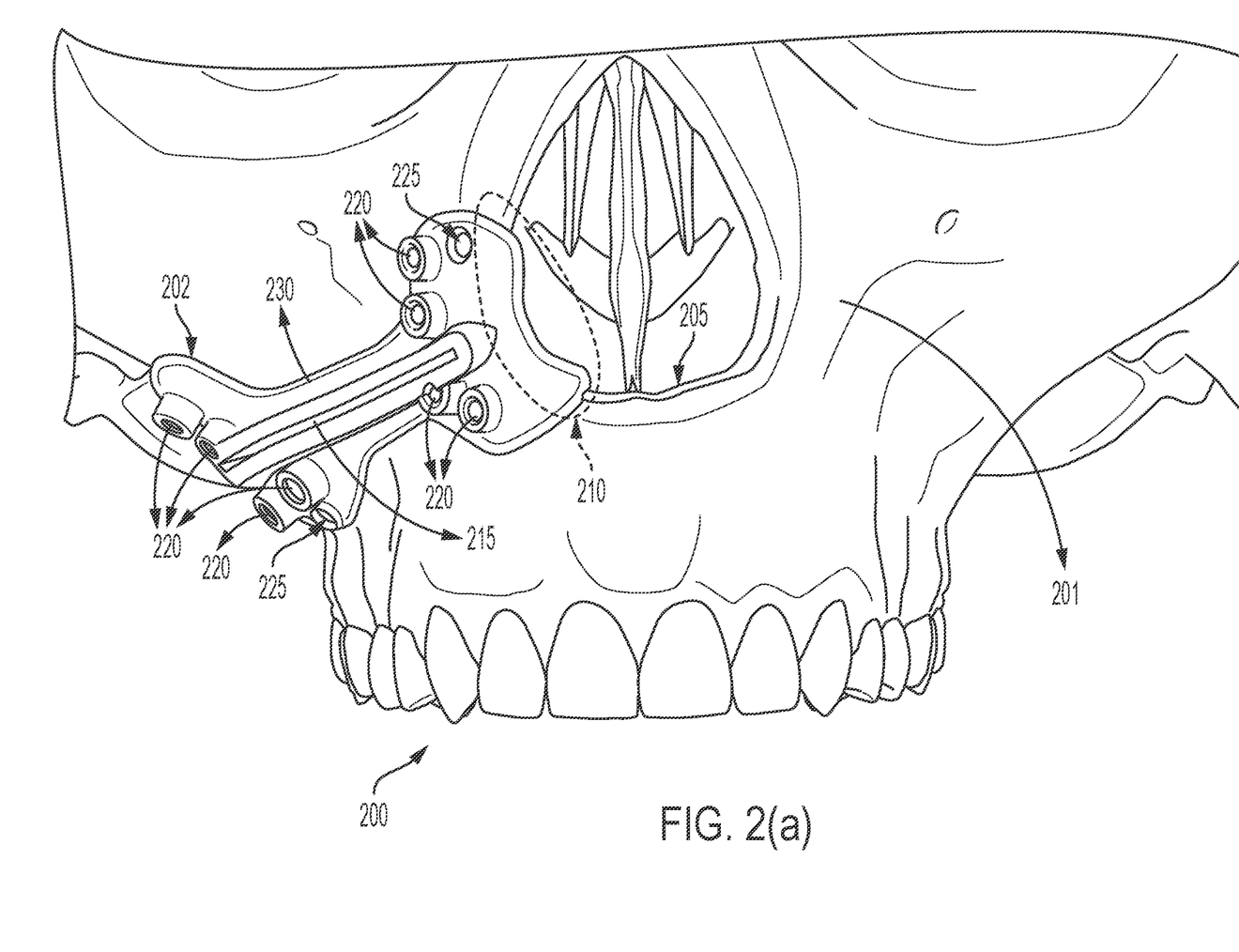
FIG. 2(a) depicts a 3D rendered image of a portion of a maxilla bone with a cutting guide placed thereon, which is formed in accordance with embodiments of the present disclosure.
Figure 2B:
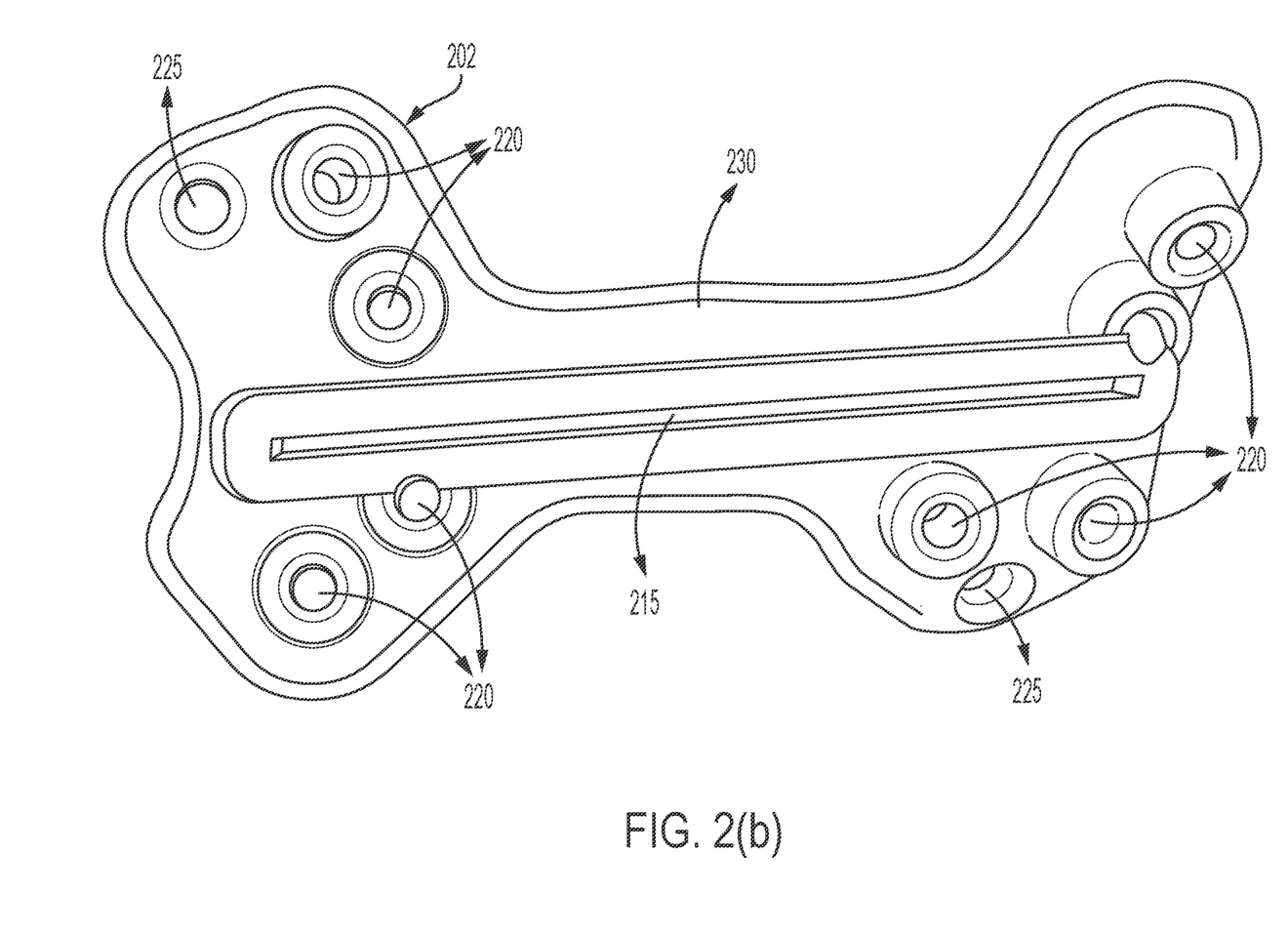
FIG. 2(b) depicts a front view of a guide, in accordance with embodiments of the present disclosure.
Figure 2C:
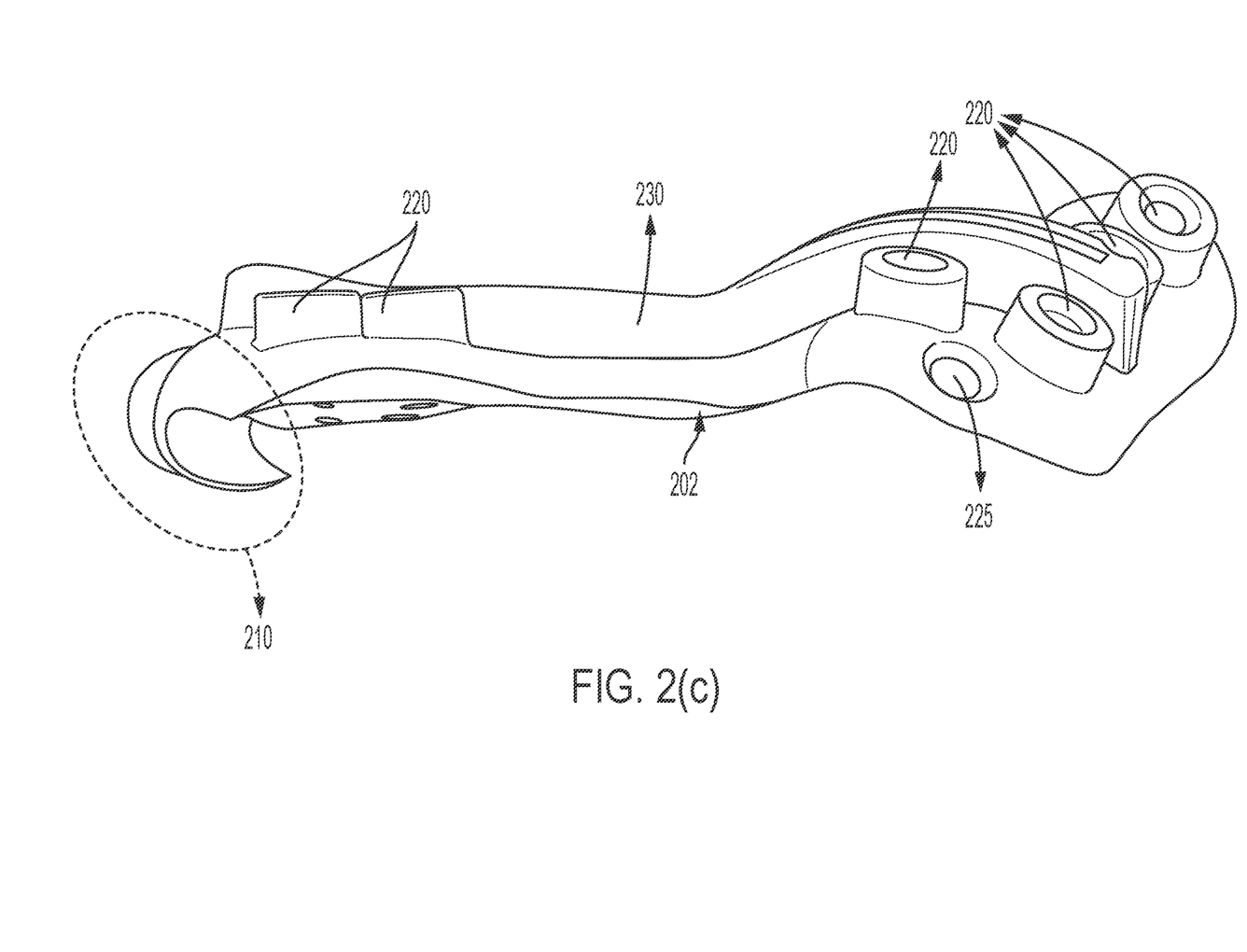
FIG. 2(c) depicts a side view of a guide, in accordance with embodiments of the present disclosure.

Referring now to FIG. 2(a), a 3D rendered image 200 of a portion of maxilla bone 201 is shown. Image 200 depicts anterior nasal aperture 205 (or the aperture 205) that may be chosen to act as a reference location or an anatomical landmark during the osteotomy surgical procedure of the maxilla bone 201. This choice may be made by a surgeon or other surgical planning technician based on any number of factors (e.g. common usage, readily recognizable landmarks, areas that a guide may easily fit as described below, and the like). Image 200 depicts an illustrative guide 230 that includes a contact surface 202 (not shown in FIG. 2(a), but is depicted in FIG. 2(c)) that conforms to at least a portion of a surface of a biological structure, such as the underlying maxilla bone 201. The guide 230 also includes a portion 210, which is designed to conform around an edge portion of the aperture 205 to at least partially secure guide 230 against maxilla bone 201. The portion 210, in embodiments, may be designed to attach (or latch) guide 230 to the aperture 205 without using fixating devices (e.g., wires or surgical screws). Such an attachment may be implemented using a fitted technique such as a form fit, friction fit, and the like. Additionally, the attachment may utilize a snap fit where a guide is snapped into a portion of a landmark surface.

In some embodiments, guide 230 may be secured around the edge portion of the aperture 205 by a friction fit. Achieving a friction fit may require applying some force to the portion 210 against the aperture 205 during the surgery. The force may be applied by hands or using a surgical tool (e.g., surgical hammer). In other embodiments, guide 230 may be secured around the edge portion of the aperture 205 through other kinds of fits, such as a clearance fit. Examples of clearance fits include loose running fit, easy running fit, close running fit, etc. Achieving a clearance fit may require less force than a friction fit. The guide design is not limited to achieving a friction or clearance fit. Other designs where the guide can extend around a portion of an anatomical landmark on a biological structure to at least partially secure the surgical cutting guide to the biological structure may be used.

In some embodiments, the contact surface 202 may be designed to follow at least a portion of the contour of the operated bone. In aspects, at least a portion of the contour of the contact surface 202 may be viewed as "a mirror image" or "a negative" or a "reverse contour" of the surface of the underlying maxilla bone 201. The imitating structure/design of the contact surface 202 of the portion 210 may help ensure proper positioning and orientation (e.g., during initial placement) of the cutting guide 230. Referring to FIG. 2(c), which depicts a side view of the guide 230 contact surface 202 of portion 210 is shown as an arcuate shaped surface which securely holds guide 230 against the aperture 205 during initial placement of guide 230 on maxilla bone 201. Portion 210, as shown in FIG. 2(c), extends backwards inside aperture 205 and is designed to hold onto the aperture 205. Once guide 230 is placed around the aperture 205, guide 230 is designed to follow and imitate the shape of the underlying maxilla bone 201, and guide 230 is automatically positioned at the desired location on maxilla bone 201 where the surgeon wants to operate. Stated yet another way, once the guide 230 is placed around the aperture 205, the guide automatically positions itself at the desired location on the bone with high precision. As is further described below, guide 230 holds itself to the aperture 205 in a manner that allows a surgeon to fixedly attach guide 230 to the underlying maxilla bone 201 and utilize guide 230 for performing a procedure to the underlying bone.

In some embodiments, guide 230 is designed such that it is configured to hold onto the anatomical landmark using the portion 210 and follow the shape of the underlying bone, where a surgeon can perform a procedure without securing the guide to the underlying bone using screws or wires. In other embodiments, guide 230 is designed such that it is configured to hold onto the anatomical landmark using the portion 210 and follow the shape of the underlying bone, but the surgeon first secures the guide to the underlying bone using screws or wires and then performs the procedure. The guide 230 may define optional apertures/holes that allow the guide to secure to the underlying bone at least from one side using screws or wires. For example, the guide 230 may define optional holes, such as holes labeled with the numeral 225 that allows the guide 230 to secure to the underlying bone using screws or wires. One or more of the holes 225 may be used to anchor the guide 230 to the underlying biological structure by using anchoring screws or drill pins inserted through the one or more holes 225. Other attachment mechanisms known in the art (e.g., surgical wires) may be used to fix the guide 230 to the underlying biological structure. In some embodiments, the guide 230 defines an aperture shown as cutting slot 215, which is designed and dimensioned to receive the blade of a cutting instrument and properly orient the blade in order to make a cut during the surgical procedure. In some embodiments, the guide 230 may also define drilling holes, such as holes 220, which may, in one example, be used to produce a hole for screw insertion to fix fractured parts of the underlying bone for immobilization. The holes 220, 225, and the cutting slot 215 are more readily visible in FIG. 2(b), which depicts a front view of the guide 230.

In some procedures, a surgeon may use a sequence (or a series) of guides to perform a procedure. In such embodiments, at least one of the guides attach to the bone aperture 205 using portion 210, while the others may be affixed with the guide 230 using screws or wires. In such embodiments, guide 230 establishes a placement location for the additional guides. In some embodiments, the design of the holes that indicate drilling holes appear different than the ones that indicate securing (or fastening) holes. For example, the holes that may be used for drilling have an elevated design, whereas the holes that may be used to fasten the guide do not have an elevated design.

In some embodiments, the guide 230 may include another portion similar to the portion 210 such that the another portion is designed to conform around a different anatomical landmark than aperture 205 to at least partially secure the guide 230. Such embodiments of the guide 230 may be secured with the underlying biological structure without using any fixating devices. In aspects, the another portion may be designed to be positioned opposite to the portion 210. For example, if the portion 210 is positioned at a distal end of the guide 230, the another portion may be positioned at a proximal end opposite to the distal end. In embodiments, portion 210 and/or the another portion may be designed to be flexible to allow stretching over the underlying anatomical landmark to achieve a fit.

The difference between the size of the guides shown in FIGS. 1 and 2(a) is readily visible. As such, designing the guides keeping the nearest anatomical landmark as a reference point (or point of attachment) results in guides that are smaller in size and are less bulky. This can facilitate improvements to the overall surgical process and increase accuracy. Furthermore, guide 120 of FIG. 1 needs to be secured using wires or screws at multiple locations. In contrast, the guide 230 may not need to be fastened using screws or wires because the guide 230 is designed to hold onto the anatomical landmark and conform to the underlying bone, or may be secured using fewer attachment points than previous solutions.

Guide 230 may be formed using additive manufacturing technology (e.g., 3D printing) through successive fusion of chosen parts of powder layers applied to a worktable. In some embodiments, PA 12 (also known as Nylon 12) is used as the powder. The guides formed using PA 12 have high tensile strength, impact strength, and are able to flex without fracture. In other embodiments, other materials may be used, such as polyetheretherketone (PEEK), poly lactic acid (PLA), Poly(methyl methacrylate) (PMMA), and photo-cured resins. In some embodiments, guide 230 may be fabricated using two or more materials. In such embodiments, a portion of guide 230 may be fabricated using a material, such as PEEK, while the rest of the guide 230 may be fabricated using a different material, such as PA 12. In some embodiments, the type of material that is used to fabricate a specific portion of the guide 230 may be chosen to improve the functionality of that portion. To illustrate, the portion 210 that latches onto the anatomical landmark may be fabricated using a material that provides better grip, while the rest of the guide 230 may be fabricated using a material that readily conforms to the underlying bone. Manufacturing of the guide 230 is not limited to additive manufacturing (or rapid prototyping) technique; other manufacturing techniques may also be used. The manufacturing process that may be used to produce guide 230 is further described below.

FIG. 2(a) illustrates the use of the guide 230 for a skull portion of the human skeletal system. However, it should be appreciated that the guide 230 may be used on a variety of different biological structures, such as tissues. For example, the tissue may be, without limitation, at least one of an articular surface, cartilage, subchondral bone and/or other tissue surface and shape.

Figure 3:
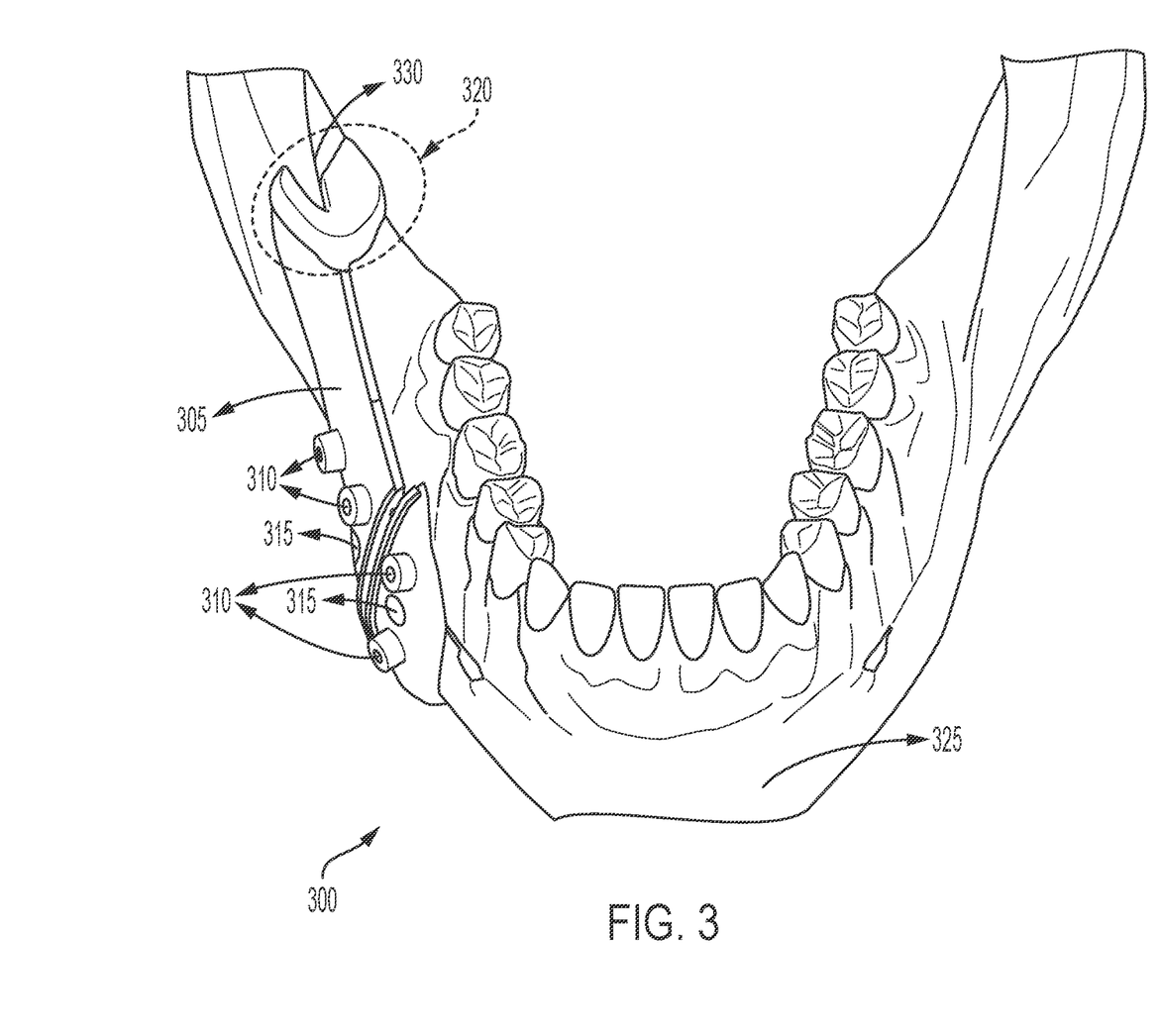
FIG. 3 depicts a 3D rendered image of a portion of a mandible bone with a cutting guide placed thereon, which is formed in accordance with embodiments of the present disclosure.

Referring now to FIG. 3, another example where an anatomical landmark is used to secure a guide is shown. FIG. 3 depicts a 3D rendered image 300 of a portion of mandible bone 325 with a guide 305 placed thereon. The image 300 depicts the anterior aspect of the coronoid process 330 (hereinafter referred to as coronoid process structure 330) that may be chosen by a surgeon or technician before the surgery to act as a reference location or an anatomical landmark during an osteotomy surgical procedure of the mandible bone 325. Selecting the coronoid process structure 330 as the anatomical landmark accurately provides the height of the mandibular foramen, where a horizontal osteotomy should be performed. FIG. 3 depicts an illustrative guide 305 that is designed to latch onto (or attach to) to coronoid process structure 330 via a portion 320 of the guide 305. The portion 320 is designed to conform to the shape of coronoid process structure 330. The portion 320 fits with coronoid process structure 330 such that the rest of the portion of the guide 305 lays at a desired location on the mandible bone 325. Stated another way, once the guide 325 is attached to coronoid process structure 330, the surgeon can position the guide 305 to the underlying mandible bone 325 where the surgeon wants to operate. In some embodiments, a surgeon can perform an osteotomy procedure on the mandible bone 325 without securing the guide 305 to the underlying bone using screws or wires. In other embodiments, the guide 305 may define optional holes, such as holes 315 that allows the guide 305 to secure to the underlying bone using screws or wires. In some embodiments, the guide 305 defines an aperture shown as a cutting slot (not expressly shown in FIG. 3).

Embodiments described in FIGS. 2(*a*) and 3 may provide for patient-specific guides, where the anatomical landmarks used as reference points are also patient-specific. In some cases, embodiments described in FIGS. 2(*a*) and 3 may provide for guides which are not patient specific, meaning that the guides are not designed for a specific patient, but are designed in accordance with specific anatomical landmarks generally found in the human anatomical structure. Thus, the same design can be used to produce multiple guides, which can further be used during osteotomy procedures of different patients. In some embodiments, these non-patient-specific guides may be designed based on age, gender, or generic physical makeup of the human anatomical structure. As such, the non-patient-specific guides may come in different sizes, e.g., small-male, small-female, medium-male, medium-female, large-male, and large-female. By way of example, a medium-male design may be used during an osteotomy procedure of a 5 foot 6 inch, 30 year old man, whereas, a large-male design may be used during an osteotomy procedure of a 6 foot, 30 year old man.

Figure 4:
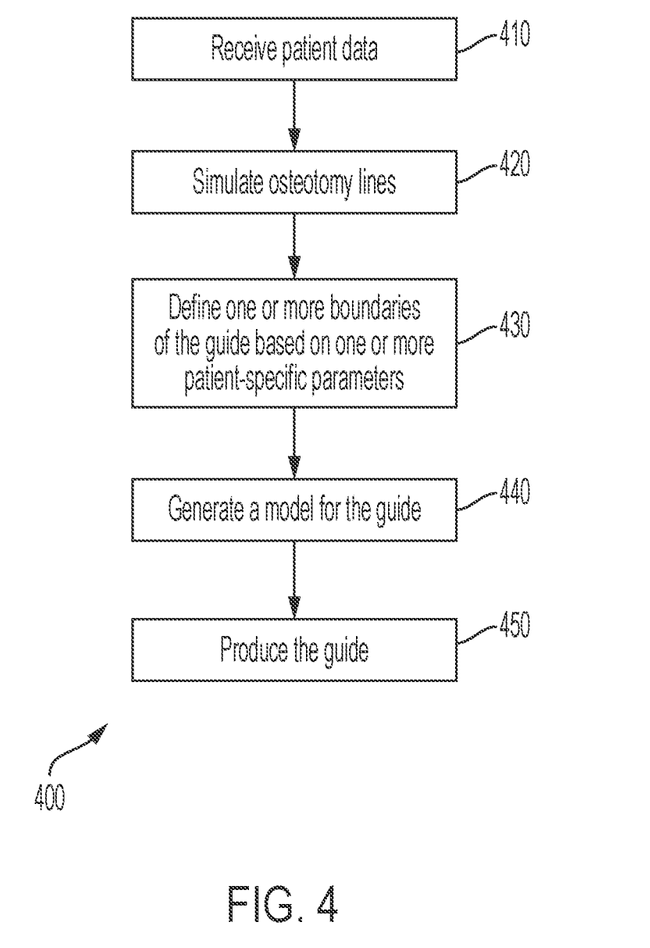
FIG. 4 depicts an illustrative method for designing and manufacturing patient-specific guides, in accordance with embodiments of the present disclosure.

FIG. 4 depicts an illustrative method 400 that may be used to design and manufacture the aforementioned patient-specific anatomical landmark guides. In some cases, method 400 may be performed, without limitation, by a medical institution (e.g., a hospital) where the surgery will eventually take place. In other cases, method 400 may be performed by a contracted third party (e.g., a medical device company) that works with the medical institution to generate and manufacture patient-specific guides.

In some embodiments, method 400 begins with block 410 that includes receiving a patient's data. The patient's data may be received by a computer system and stored in a computer-readable medium in the computer system. Patient-specific information is advantageously used to ensure that the guides appropriately conform to the surface of the underlying biological structure. Patient-specific information, in some examples, includes one or more electronic images and/or measurements of the surface of the desired biological structure. Images and measurements of the surface of the biological structure, in one example, may provide coordinates that define the surface and shape of the biological structure. The electronic images of the tissue may be from, without limitation, a CT image, a spiral CT image, an MRI image, an ultrasound scan, digital tomosynthesis, or optical coherence tomography. In some embodiments, the coordinates of the biological structure may be utilized to shape at least some of the portions of the guide. The received patient data, in one embodiment, may then be utilized to generate a 3D bone model of the portion of the body where the surgery is to be performed. The 3D bone model may then be subsequently used in surgical planning by the surgeon performing the procedure. The 3D bone model, in one embodiment, is generated using the computer system configured to receive the images and/or other details and generate the bone model using a software system installed in the computer system.

Method 400 may then move to block 420 that includes simulating, in the computer system, osteotomy lines on the 3D bone model of the patient. In one embodiment, a user (e.g., medical device technician) defines the cutting planes of the bone on which the surgeon wants to operate. In some cases, the surgeon may first virtually operate on the desired bone to the find the optimal anatomical landmark near the desired area. In other cases, the surgeon may identify the optimal anatomical landmark without virtually operating on the desired bone.

Once the optimal anatomical landmark and the desired portion of the bone is identified, the method 400 may then move to block 430 that includes defining one or more boundaries of a guide. The boundaries of the guide, in some embodiments, are based on one or more input parameters. In some embodiments, the user of block 410 extrapolates relevant input parameters from the images and/or other details received in block 410. In some embodiments, the parameters may include the information related to the anatomical landmark. For example, the parameter may include the length of extension needed to precisely conform and strongly latch onto the anatomical landmark. Other parameters may include minimum and maximum thickness of the desired bone, size of the osteotomy line, and the size of the holes (drilling and affixing).

After defining the boundaries, the user may instruct the computer system to generate a 3D model for the guide at block 440. The user may also instruct the computer system to store the 3D model for the guide in the computer-readable medium. Before producing the guide, the user may access the stored 3D model from the computer-readable medium. This 3D model may then be used to manufacture and produce the guide (block 450). In some cases, the 3D model may first sent to the surgeon for his approval, and following his approval, a guide is manufactured. In one embodiment, the guide is manufactured using additive technology or freeform fabrication. In this method of manufacture, the guides are formed through successive fusion of chosen parts of powder layers applied to a worktable. In some embodiments, PA 12 (also known as Nylon 12) is used as the powder. The guides formed using PA 12 have high tensile strength, impact strength, and are able to flex without fracture. In other embodiment, other type of material may be used. In summary, once the patient-specific information is ascertained, rapid prototyping or other manufacturing techniques may be used to adapt the guide to the patient's particular biological structure. In some embodiments, a mold may be made to form the guide. In some embodiments, a guide may be manufactured using a 3D printing technology disclosed in co-pending U.S. patent application Ser. No. 16/378,446, entitled System and Method for Forming Material Layers for Surgical Applications, and filed by the assignee of the present application on Apr. 8, 2019. The disclosure of U.S. patent application Ser. No. 16/378,446 is incorporated by reference herein in its entirety.

The guide manufactured using the techniques described above may be disposed in a packaging unit. The packaging unit may include a contoured unit having a contoured surface that matches a contour of the biological structure (e.g., bone, such as maxilla bone) on which a surgeon would operate. The contoured unit may be 3D printed using metal, plastic, poly-ether-ether-ketone (PEEK) material, etc. in a same or similar manner as described in U.S. patent application Ser. No. 16/378,446. As such, a guide may be disposed onto the contoured unit and provide a visual aid to the surgeon before the surgery. In some embodiments, the contoured unit also has one or more features that would further facilitate the surgery by providing a visual aid to the surgeon. For example, the contoured unit may have one or more features, such as apertures, which may be holes for receiving surgical screws that are selected based on thickness/depth of bone exhibiting the contour in the 3D model of the desired bone of a patient. Additionally, the contoured unit may be a part of a surgical kit that includes other medical devices (e.g., bone plates) that may be used during the surgery. In some embodiments, the packing unit includes a lid that may have a reverse contour, which is designed to mate with the contour of the surface of the contoured unit in such a way that the contoured unit and the guide(s) and/or other medical devices (e.g., bone plates and surgical screws) are secured in place when the lid is connected to the contoured unit.

Figure 5:
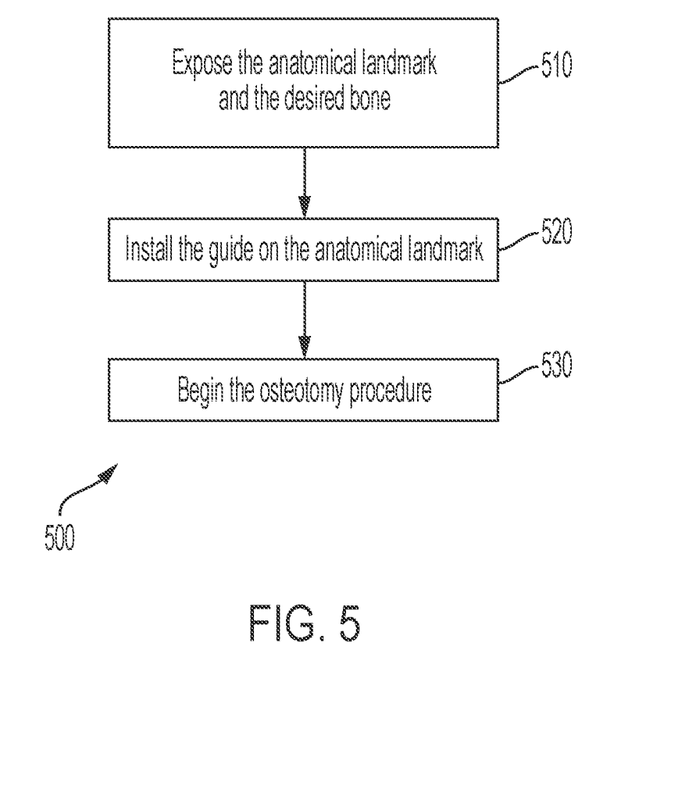
FIG. 5 depicts an illustrative method that may be implemented by a surgeon during an osteotomy procedure, in accordance with various embodiments of the present disclosure.

The steps described in FIG. 4 may be adapted and used to design and manufacture non-patient specific anatomical landmark guides. For example, for non-patient specific guides, block 410 may include receiving a reference patient's data (e.g., one or more electronic images and/or measurements of the surface of the desired biological structure). The reference patient, as noted above, may be chosen based on certain demographic characteristics. The coordinates that define the surface and shape of the reference biological structure may be extracted using the reference patient's data. Similar to block 410, the coordinates of the reference biological structure may be utilized to shape at least some of the portions of the guide. In aspects, the coordinates may then be utilized to generate a reference 3D bone model for the reference biological structure. In embodiments, the reference bone 3D model may then be used to simulate osteotomy lines. A user (e.g., surgeon or technician) may identify a reference anatomical landmark based on the reference biological structure. Once the reference anatomical landmark is identified, one or more boundaries of a guide are defined. The boundaries of the guide, in some embodiments, may be based on one or more input parameters extrapolated from the reference patient's data. In some embodiments, the parameters may include the reference thickness of the operated bone, size of the osteotomy line, and the size of the holes (drilling and affixing). After defining the boundaries, the user may instruct the computer system to generate a 3D model for the guide. This 3D model may then be used to manufacture and produce the guide using the process described above. Referring now to FIG. 5, an illustrative method 500 that may be implemented by a surgeon using the aforementioned guides during an osteotomy procedure is shown. In one embodiment, method 500 begins with block 510 that includes exposing the landmark and the desired bone by using relevant surgical techniques. The method 500 may then move to block 520 that includes installing the guide on the anatomical landmark. The surgeon may first carefully place the guide on the anatomical landmark, and due to the design of the guide, the guide may conform to both the anatomical landmark and the desired bone. In some cases, the surgeon may determine that the guide needs to be secured using wires or screws. As such, the surgeon may secure the guide with the underlying bone via the holes defined for securing the guide. Once the guide is installed, the method 500 may move to the block 530 that includes beginning the osteotomy procedure. Based on the type of procedure, the osteotomy procedure may include different steps.

FIGS. 4 and 5 describe manufacturing and using patient-specific guides. However, it would be readily apparent for one skilled in the art to modify the methods described in FIGS. 4 and 5 and manufacture and use non-patient-specific guides that are designed in accordance with specific anatomical landmarks found in the human body.

Although embodiments of the present application and its advantages have been described in detail, it should be understood that various changes, substitutions and alterations can be made herein without departing from the spirit and scope of the invention as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure of the present invention, processes, machines, manufacture, compositions of matter, means, methods, or steps, presently existing or later to be developed that perform substantially the same function or achieve substantially the same result as the corresponding embodiments described herein may be utilized according to the present invention. Accordingly, the appended claims are intended to include within their scope such processes, machines, manufacture, compositions of matter, means, methods, or steps. Moreover, the scope of the present application is not intended to be limited to the particular embodiments of the process, machine, manufacture, composition of matter, means, methods and steps described in the specification.

The invention claimed is:

1. A surgical cutting guide, comprising:
a contact surface having a contour that matches a reverse contour of a biological structure, wherein the biological structure includes a bone having a length, a width, and a thickness, wherein the thickness is less than the length and the width;
a longitudinal axis extending between a proximal end and a distal end;
an extension portion at the distal end, the extension portion comprising a hook extending along the longitudinal axis, the hook configured to extend around an edge of an anatomical landmark on the biological structure, the hook having a hook width sized to extend around the thickness of the bone at the edge of the anatomical landmark so as to latch the surgical cutting guide onto the anatomical landmark with a remainder of the guide extending along the reverse contour of the biological structure away from the anatomical landmark;
one or more apertures defined on the surgical cutting guide; and
a cutting slot extending from the proximal end to the distal end.

2. The surgical cutting guide of claim 1, wherein the one or more apertures include holes that are configured to receive surgical screws that secure the surgical cutting guide on the biological structure.

3. The surgical cutting guide of claim 2, wherein the one or more apertures include holes that are configured to facilitate drilling holes in the biological structure.

4. The surgical cutting guide of claim 1, wherein the biological structure includes a maxilla bone and the anatomical landmark includes a portion of a nasal aperture near the maxilla bone.

5. The surgical cutting guide of claim 1, wherein the biological structure includes a mandible bone and the anatomical landmark includes a coronoid process structure.

6. The surgical cutting guide of claim 1, wherein the contour and the extension portion are custom-matched based on imaging data of the biological structure.

7. The surgical cutting guide of claim 1, wherein the one or more apertures are positioned on the proximal end.

8. The surgical cutting guide of claim 7, wherein the one or more apertures include holes that are configured to receive surgical screws that secure the surgical cutting guide on the biological structure at the proximal end.

9. The surgical cutting guide of claim 1, wherein the proximal end has a second extension portion that is configured to extend around a portion of a second anatomical landmark on the biological structure, and wherein said second extension portion is also configured to at least partially secure the surgical cutting guide to the biological structure.

10. A medical apparatus, comprising:
a cutting guide three-dimensionally (3D) printed based on an anatomical landmark positioned near a biological structure that is to be operated, the biological structure including a bone having a length, a width, and a thickness, wherein the thickness is less than the length and the width, wherein the cutting guide comprises:
a contact surface having a contour that matches at least some of a reverse contour of the biological structure;
a longitudinal axis extending between a proximal end and a distal end;
an extension portion at the distal end, the extension portion comprising a hook extending along the longitudinal axis, the hook configured to extend around an edge of the anatomical landmark on the biological structure, the hook having a hook width sized to extend around the thickness of the bone at the edge of the anatomical landmark so as to latch the surgical cutting guide onto the anatomical landmark with a remainder of the guide extending along the reverse contour of the biological structure away from the anatomical landmark;
one or more apertures defined on the surgical cutting guide; and a cutting slot extending from the proximal end to the distal end.

11. The medical apparatus of claim 10, wherein the extension portion is configured to secure the surgical cutting guide to the biological structure without using surgical fixating devices.

12. The medical apparatus of claim 10, wherein the one or more apertures are positioned on the proximal end.

13. The medical apparatus of claim 12, wherein the one or more apertures include holes that are configured to receive surgical screws that secure the surgical cutting guide on the biological structure at the proximal end.

14. A surgical cutting guide, comprising:
a contact surface having a contour that matches a reverse contour of a maxilla bone;
a longitudinal axis extending between a proximal end and a distal end;
an extension portion at the distal end, the extension portion comprising a hook extending along the longitudinal axis, the hook configured to extend around an edge of a nasal aperture near the maxilla bone, the hook having a width sized to extend around a thickness of the maxilla bone at the edge of the nasal aperture to latch the surgical cutting guide onto the nasal aperture with a remainder of the guide extending along the reverse contour of the maxilla bone away from the nasal aperture;
one or more apertures defined on the surgical cutting guide; and a cutting slot extending from the proximal end to the distal end.

15. The surgical cutting guide of claim 14, wherein the one or more apertures include holes that are configured to receive surgical screws that secure the surgical cutting guide on the maxilla bone.

16. The surgical cutting guide of claim 14, wherein the contour and the extension portion are custom-matched based on imaging data of the maxilla bone.

17. The surgical cutting guide of claim 14, wherein the one or more apertures are positioned on the proximal end.

18. The surgical cutting guide of claim 17, wherein the one or more apertures include holes that are configured to receive surgical screws that secure the surgical cutting guide on the maxilla bone at the proximal end.

19. The surgical cutting guide of claim 1, wherein the cutting slot is configured to receive a blade of a cutting instrument.

20. The surgical cutting guide of claim 1, wherein a width of the cutting slot is smaller than a length of the cutting slot.

* * * * *

UNITED STATES PATENT AND TRADEMARK OFFICE
CERTIFICATE OF CORRECTION

| | | |
|---|---|---|
| PATENT NO. | : 12,426,902 B2 | Page 1 of 1 |
| APPLICATION NO. | : 17/006603 | |
| DATED | : September 30, 2025 | |
| INVENTOR(S) | : Devid R. Zille | |

It is certified that error appears in the above-identified patent and that said Letters Patent is hereby corrected as shown below:

In the Specification

Under Column No. 2, Line No. 44, delete "scans, MM scans," and insert --scans, MRI scans,--

Under Column No. 2, Line No. 63, delete "scans, MM scans," and insert --scans, MRI scans,--

Signed and Sealed this
Twenty-fifth Day of November, 2025

John A. Squires
*Director of the United States Patent and Trademark Office*